(12) United States Patent
Nagatsuka (10) Patent No.: US 12,406,359 B2
(45) Date of Patent: Sep. 2, 2025

(54) MEDICAL INFORMATION MANAGEMENT APPARATUS, DATA STRUCTURE OF MEDICAL INFORMATION, AND STORAGE MEDIUM

(71) Applicant: Konica Minolta, Inc., Tokyo (JP)

(72) Inventor: Sumiya Nagatsuka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 375 days.

(21) Appl. No.: 17/822,031

(22) Filed: Aug. 24, 2022

(65) Prior Publication Data
US 2023/0062687 A1  Mar. 2, 2023

(30) Foreign Application Priority Data
Aug. 30, 2021  (JP) .................................. 2021-139797

(51) Int. Cl.
*G06T 7/00* (2017.01)
*G16H 30/40* (2018.01)

(52) U.S. Cl.
CPC ............ *G06T 7/0012* (2013.01); *G16H 30/40* (2018.01); *G06T 2207/30004* (2013.01)

(58) Field of Classification Search
CPC ......... G06T 7/0012; G06T 2207/30004; G06T 7/0016; G06T 2207/10116; G16H 30/40; G16H 50/20; A61B 6/52; A61B 6/5217
See application file for complete search history.

(56) References Cited

U.S. PATENT DOCUMENTS

2018/0049712 A1* 2/2018 Muraoka ................. A61B 6/461
2020/0320336 A1* 10/2020 Takata .................. A61B 6/5217

FOREIGN PATENT DOCUMENTS

| JP | 2016-174735 A | 10/2016 |
|----|---------------|---------|
| JP | 2017-018681 A | 1/2017 |
| JP | 2018-027244 A | 2/2018 |

OTHER PUBLICATIONS

JPO, Office Action for the corresponding Japanese application No. 2021-139797, dated Feb. 1, 2022, with English translation.
Office Action, dated Jul. 1, 2025, which was issued for the corresponding Japanese Application No. 2022-095658, pages, with English translation.

* cited by examiner

*Primary Examiner* — Kent Yip
(74) *Attorney, Agent, or Firm* — LUCAS & MERCANTI, LLP (57) ABSTRACT

A medical information management apparatus including a hardware processor that manages dynamic information and non-dynamic information in association with each other, the dynamic information being obtained by dynamic imaging with radiation to a first subject that satisfies a condition of a predetermined disease, and the non-dynamic information being obtained by imaging other than the dynamic imaging or a test to a second subject that satisfies the condition of the predetermined disease.

17 Claims, 5 Drawing Sheets

| | | | | | | |
|---|---|---|---|---|---|---|
| NON-DYNAMIC INFORMATION 153 | ⋮ | ⋮ | ... | ... | ... | ... |
| | SPIROMETRY TEST | TEST RESULT | *** | *** | ... | ... |
| | SCINTIGRAPHY | MEASURED VALUE | *** | *** | ... | ... |
| | | FINDING | *** | *** | ... | ... |
| | | MEDICAL IMAGE | *** | *** | ... | ... |
| | MRI | MEASURED VALUE | *** | *** | ... | ... |
| | | FINDING | *** | *** | ... | ... |
| | | MEDICAL IMAGE | *** | *** | ... | ... |
| | CT | MEASURED VALUE | *** | *** | ... | ... |
| | | FINDING | *** | *** | ... | ... |
| | | MEDICAL IMAGE | *** | *** | ... | ... |
| DYNAMIC INFORMATION | MOVEMENT INFORMATION | ⋮ | ... | ... | ... | ... |
| | | AIRWAY DIAMETER STENOSIS RATE | *** | *** | ... | ... |
| | | LUNG FIELD AREA CHANGE RATE | *** | *** | ... | ... |
| | | DIAPHRAGM SPEED | *** | *** | ... | ... |
| | DYNAMIC IMAGE | | A | B | ... | ... |
| HOSPITAL INFORMATION | | | *** | *** | ... | ... |
| IMAGING SITE | | | *** | *** | ... | ... |
| ATTRIBUTE INFORMATION | | | *** | *** | ... | ... |
| DISEASE INFORMATION | | | *** | *** | ... | ... |

MEDICAL INFORMATION MANAGEMENT APPARATUS, DATA STRUCTURE OF MEDICAL INFORMATION, AND STORAGE MEDIUM

CROSS-REFERENCE TO RELATED APPLICATIONS

The entire disclosure of Japanese Patent Application No. 2021-139797 filed on Aug. 30, 2021 is incorporated herein by reference in its entirety.

BACKGROUND

Technological Field

The present invention relates to a medical information management apparatus, a data structure of medical information, and a storage medium.

Description of the Related Art

Typically, a diagnosis method for detecting an abnormality such as a lesion by comparing a current image with an image obtained by radiographing a patient in the past is used. However, an image of a normal case (hereinafter, referred to as a normal image) in the past for a diagnosis target patient does not always exist, and thus, a technique of extracting an image having a normal structure similar to a normal structure of the diagnosis target patient from a large-scale database constituted with normal images and using a similarity difference image which indicates a difference between the extracted normal image and an image of the diagnosis target patient (hereinafter, referred to as a diagnosis target image) as a diagnosis assistance image has been proposed (see JP 2016-174735A). However, a shape of an organ varies between individuals, which causes artifact in the similarity difference image, and thus, the similarity difference image is generated in a case where a shape of an organ in the normal image within the image database matches a shape of an organ in the diagnosis target image.

By the way, the above-described related art relates to a radiographic still image, and use of an image obtained by radiographing at a maximal expiratory level is known as an example of a normal image of a still image. Meanwhile, while a diagnosis using a dynamic image (dynamic information) obtained through dynamic imaging with radiation is tried in recent years, what kind of dynamic image is a normal image is not sufficiently comprehended, and thus, a dynamic image is also determined on the basis of knowledge about a normal image of a still image.

However, there is a case where a large difference cannot be found in a shape of a structure such as an organ and a bone in an image at a maximal expiratory level between a normal image and an image of a patient having a disease, and there is a problem that a doctor cannot sufficiently make a diagnosis using a dynamic image only with knowledge about a normal image of a still image.

Further, an information amount of a dynamic image is significantly larger than an information amount of a still image, and thus, importance of a normal image which becomes a diagnosis criterion increases.

Further, a dynamic image, which is a moving image, requires more time for viewing than a still image. Viewing of all frames of a moving image leads to rapid increase in man-hours of a doctor, which is unacceptable. It is therefore necessary to achieve viewing efficiency and diagnostic efficiency of a doctor in a dynamic state compared to a still image. This requires diagnosis support such as analysis of moving image data, marking of candidates for abnormal parts and informing by highlighting, or the like. Extraction, or the like, of candidates for abnormal parts for the purpose of such diagnosis support requires a normal image, and thus, collection of normal images becomes more important in a moving image than in a still image.

SUMMARY

However, because dynamic imaging is a new technology, the number of data on normal and abnormal cases is small, and few physicians have knowledge of dynamic image and analysis.

There is also a desire to browse dynamic information by comparing it with information obtained by conventional diagnostic methods other than dynamic imaging (medical images taken with other modalities, test results, etc.).

In addition, in order to promote the dynamic state widely, normal and abnormal cases should be made widely available for browsing and downloading to educate users and stimulate further research. Quantitative diagnostic criteria (standard values) for the dynamic image are also necessary to promote the diagnosis of the dynamic state. Thus, in order to promote the use of the dynamic image, it is necessary to deepen the understanding of the dynamic image and to accumulate the dynamic image in an easily accessible form.

The present invention has been made in consideration of the above problems in conventional techniques, and an object of the present invention is to facilitate the use of dynamic information.

To achieve at least one of the abovementioned objects, according to an aspect of the present invention, a medical information management apparatus reflecting one aspect of the present invention is a medical information management apparatus including a hardware processor that manages dynamic information and non-dynamic information in association with each other, the dynamic information being obtained by dynamic imaging with radiation to a first subject that satisfies a condition of a predetermined disease, and the non-dynamic information being obtained by imaging other than the dynamic imaging or a test to a second subject that satisfies the condition of the predetermined disease.

To achieve at least one of the abovementioned objects, according to another aspect of the present invention, a data structure of medical information reflecting one aspect of the present invention is a data structure of medical information that is used in a medical information management apparatus, the data structure including: dynamic information data which is obtained by dynamic imaging with radiation to a first subject that satisfies a condition of a predetermined disease; and non-dynamic information data which is obtained by imaging other than the dynamic imaging or a test to a second subject that satisfies the condition of the predetermined disease, the non-dynamic information data being associated with the dynamic information data.

To achieve at least one of the abovementioned objects, according to another aspect of the present invention, a data structure of medical information reflecting one aspect of the present invention is a non-transitory computer-readable storage medium storing a medical information management program causing a computer to perform management processing which is managing dynamic information and non-dynamic information in association with each other, the dynamic information being obtained by dynamic imaging with radiation to a first subject that satisfies a condition of a predetermined disease, and the non-dynamic information being obtained by imaging other than the dynamic imaging or a test to a second subject that satisfies the condition of the predetermined disease.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, embodiments of a medical information management apparatus, a data structure of medical information, and a medical information management program according to the present invention will be described with reference to the drawings. However, the scope of the invention is not limited to the disclosed embodiments or illustrated examples.

[Configuration of Medical Information Management System]

Figure 1:
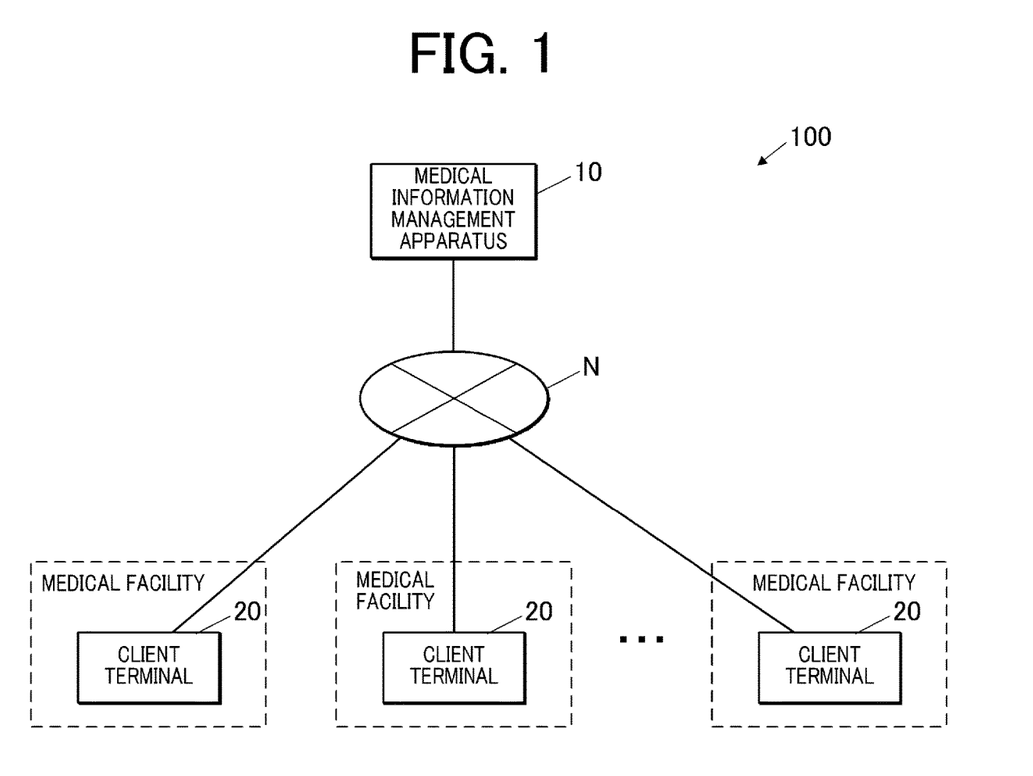
FIG. 1 is a view showing a system configuration of a medical information management system in an embodiment of the present invention.

FIG. 1 shows the system configuration of a medical information management system 100 in an embodiment of the present invention.

As shown in FIG. 1, the medical information management system 100 is configured by including a medical information management apparatus 10, and client terminals 20 used by medical workers belonging to respective medical facilities. The medical information management apparatus 10 and the client terminals 20 are connected via a communication network N to enable data communication.

The medical information management apparatus 10 stores and manages medical information uploaded from the client terminal 20. The medical information management apparatus 10 provides medical information to the requesting client terminal 20 in response to a browsing request from the client terminal 20. The medical information management apparatus 10 may be a cloud server.

The medical information includes dynamic information and non-dynamic information.

The dynamic information is information obtained by dynamic imaging to the subject, and includes at least one of a dynamic image (medical image obtained by dynamic imaging) and movement information.

Dynamic imaging is imaging of dynamic states, such as the morphological changes of lung expansion and contraction associated with respiratory motion, and the beating of the heart. In dynamic imaging, multiple images showing the dynamic state of the subject are obtained by repeatedly emitting pulsed radiation such as X-rays to the subject at predetermined time intervals (pulsed irradiation) or by continuously emitting the radiation at low dose without interruption (continuous irradiation). Dynamic imaging includes imaging of moving image, but does not include imaging of still images while the moving image is displayed (fluoroscopic imaging).

The dynamic image is a series of images (image data) obtained by dynamic imaging. Each of the multiple images forming the dynamic image is referred to as a frame image. The dynamic image includes the moving image, but does not include the image obtained by imaging of still images while the moving image is displayed.

The movement information is information that represents the movement of the subject (respiratory, cardiovascular, orthopedic, swallowing-related tissues, etc.) obtained by analyzing the dynamic image (medical image obtained by dynamic imaging). The movement information includes the position obtained for each frame image, the speed obtained from the difference between the frame images, and the maximum speed and rate of change in size obtained analytically from such information. The movement information includes, for example, diaphragm speed, lung field area change rate, airway diameter stenosis rate, and other information that quantifies tissue movement.

The non-dynamic information is information obtained by imaging other than dynamic imaging or test on the subject, and includes information obtained from CT, scintigraphy, MRI, spirometry, reports (radiographic reading reports, test reports, etc.), etc.

The non-dynamic information includes medical images obtained by imaging other than dynamic imaging (the non-dynamic image). The medical images in the non-dynamic information include at least one of the first medical image (radiographic image) obtained from at least one of still imaging and fluoroscopic imaging by radiation, and the second medical image (non-radiographic image) obtained from non-radiographic imaging (imaging other than radiation imaging).

Still imaging includes simple radiography, CT, and scintigraphy.

Fluoroscopic imaging takes still images while displaying fluoroscopic moving image of organs, bones, and other parts of the body by using radiation.

The non-radiographic imaging is MRI, etc.

The non-dynamic information includes at least one of the test results (e.g., measurements, measured values) and the test reports (reports on the tests) which are obtained from tests not accompanied by images.

The tests not accompanied by images include spirometry and pulse oximeter ($SpO_2$: transcutaneous arterial blood oxygen saturation) tests.

The client terminal 20 is a computer device such as a PC (Personal Computer), and a tablet terminal used in each medical facility. The client terminal 20 uploads, to the medical information management apparatus 10, the medical image (dynamic image/non-dynamic image) obtained by imaging of a patient in the medical facility and medical information such as test results obtained by the test on the patient, and displays medical information stored in the medical information management apparatus 10.

Figure 2:
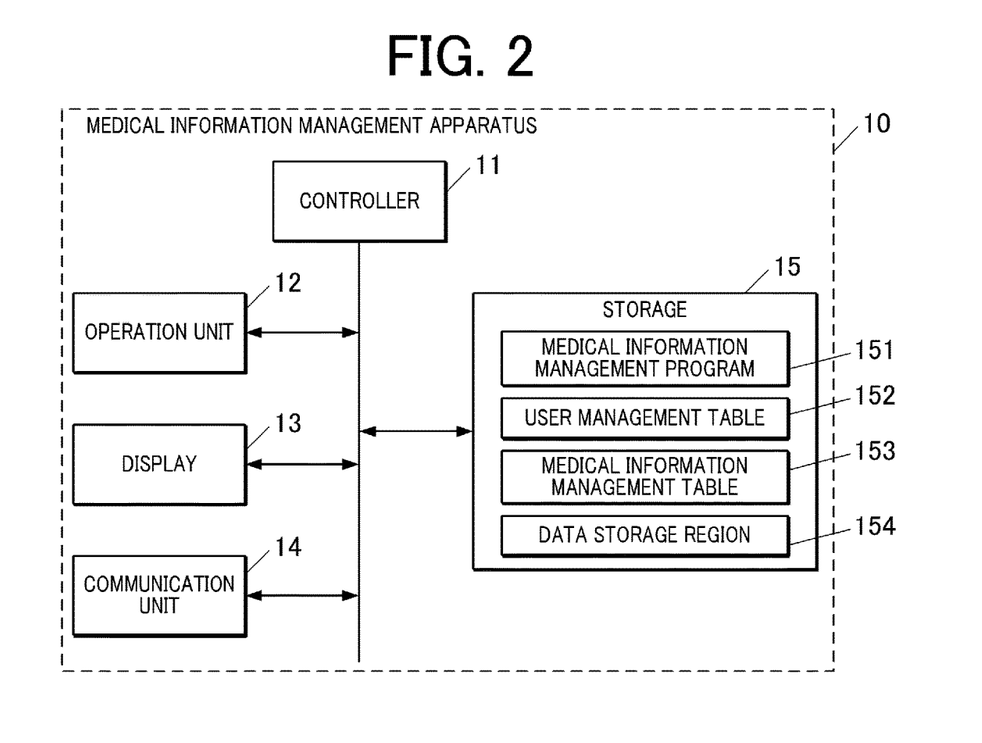
FIG. 2 is a block diagram showing the functional configuration of a medical information management apparatus.

FIG. 2 shows the functional configuration of the medical information management apparatus 10.

As shown in FIG. 2, the medical information management apparatus 10 is configured by including a controller 11 (hardware processor), an operation unit 12, a display 13, a communication unit 14, a storage 15, etc. The components are connected via a bus.

The controller 11 is configured by including a CPU (Central Processing Unit), a RAM (Random Access Memory), etc., and integrally controls the processing operations of the components in the medical information management apparatus 10. The CPU of the controller 11 reads out system programs and various processing programs stored in the storage 15 to loads them into the RAM, and executes various processing in accordance with the loaded programs.

The operation unit 12 is configured by including a keyboard including cursor key, character and numeral input keys and various function keys, and a pointing device such as a mouse. The operation unit 12 outputs the instruction signals input by the key operation to the keyboard and mouse operation to the controller 11.

The display 13 is configured by a monitor such as an LCD (Liquid Crystal Display), and displays various screens in accordance with the instruction of the display signal input from the controller 11.

The communication unit 14 is configured by a network interface or the like, and performs data transmission and reception with external devices connected via the communication network N such as the internet.

The storage 15 is composed of HDD (Hard Disk Drive), SSD (Solid State Drive), etc., and stores various processing programs, parameters and files necessary for execution of said programs, etc. For example, the storage 15 stores a web server program to realize a function as a web server that communicates with a web browser installed in the client terminal 20 using the HTTP protocol to provide various web screens to the web browser, application programs that run on the web server, etc.

The storage 15 stores a medical information management program 151, a user management table 152, and a medical information management table 153. The storage 15 also stores a data storage region 154.

The user management table 152 is a table for managing the access range of the user for each user (medical worker) that uses the medical information management system 100.

Figure 3:
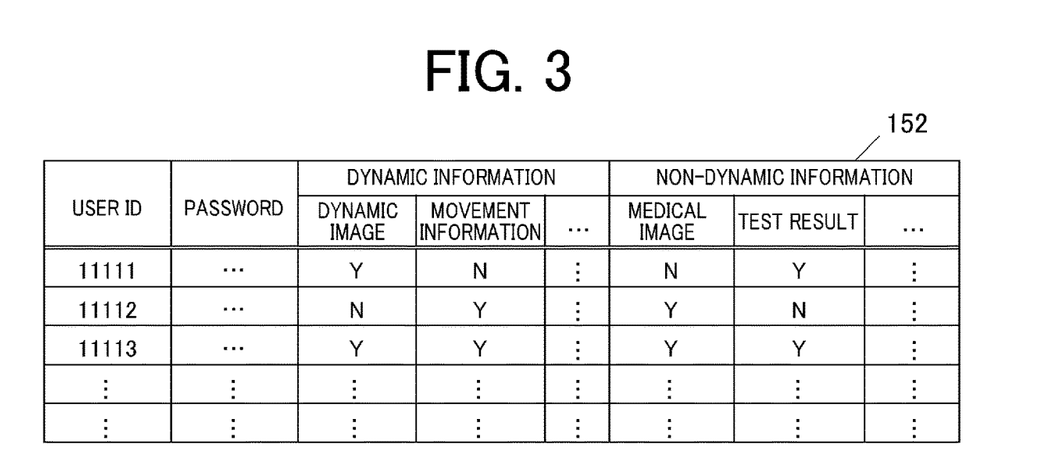
FIG. 3 is a view showing a data structure example of a user management table.

FIG. 3 shows a data structure example of the user management table 152.

In the user management table 152, for each user, the user ID, the password, the access authority to the dynamic image, the access authority to the movement information, the access authority to the medical image (non-dynamic image) in the non-dynamic information, the access authority to the test result, etc. are associated with each other. When the term of "medical image" is used for the medical image included in the non-dynamic information, the term of "medical image" is used to mean a non-dynamic image, and does not include the dynamic image.

The user ID is identification information of the user.

The password is used for user authentication when the user logs in the system.

In each item (dynamic image, movement information, medical image, test result, etc.) of the user management table 152, "Y" indicates having the access authority, and "N" indicates not having the access authority.

The medical information management table 153 is a table for managing medical information, and prepared in advance.

The medical information managed in the medical information management table 153 is collected from each medical facility.

Figure 4:
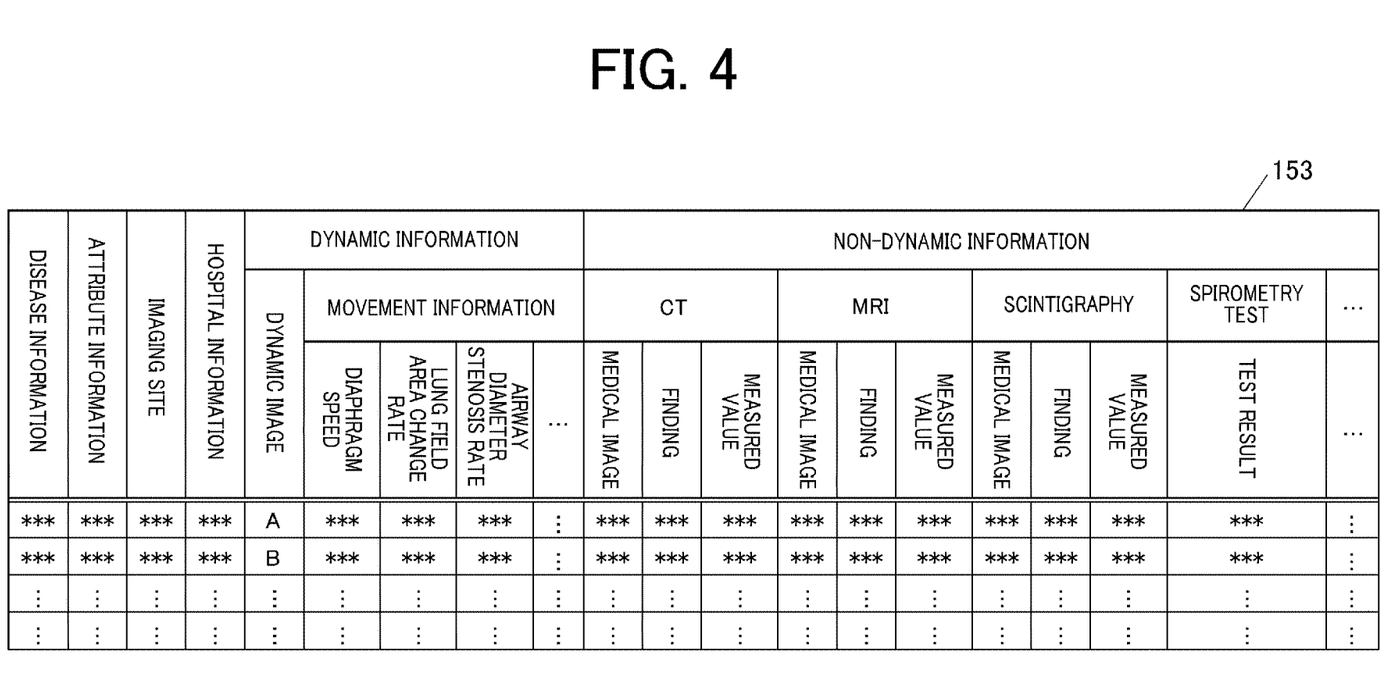
FIG. 4 is a view showing a data structure example of a medical information management table.

FIG. 4 shows a data structure example of the medical information management table 153.

In the medical information management table 153, the dynamic information and the non-dynamic information are associated with each other, for each combination of the disease information, the attribute information, the imaging side, and the hospital information.

The disease information is information on the disease that the subject has. The disease information includes COPD (chronic obstructive pulmonary disease), interstitial pneumonia, no disease, etc.

The attribute information is information indicating the attribute of the subject. The attribute information includes the gender, the birth date, the age, the height, BMI, race, history of smoking, etc. The attribute information does not include information identifying the person. The information identifying the person includes name, address, telephone number, etc.

The imaging site is information indicating the site of the imaging target. The imaging site includes the lungs, heart, vocal cords, elbows, knees, etc.

The hospital information is information regarding the hospital (medical facility) where imaging or test was performed to the subject. The hospital information includes departments such as internal medicine, orthopedics, etc., and physicians involved in imaging or testing.

The dynamic information includes the dynamic image and the movement information (diaphragm speed, lung field area change rate, airway diameter stenosis rate, etc.).

In the field of "dynamic image", identification information for identifying the dynamic image is stored. In the medical information management table 153, the "dynamic image" included in each record may be a single dynamic image or may be a dynamic image group of multiple dynamic images (group having similar movement information).

The movement information may be information obtained by the medical information management apparatus 10 analyzing the dynamic image, or may be information obtained from the external device.

The non-dynamic information includes information which was obtained for each imaging other than dynamic imaging or test.

The non-dynamic information regarding imaging such as CT, MRI, and scintigraphy includes the medical image, finding, measured value, etc.

In the field of "medical image", identification information for identifying the medical image (non-dynamic image) obtained by imaging other than dynamic imaging.

In the field of "finding", the representative finding for non-dynamic image is stored.

In the field of "measured value", the representative measured value calculated from the non-dynamic image is stored.

The non-dynamic information regarding the test not accompanied by image such as spirometry test includes the test result (measured value), etc.

In the data storage region 154, medical information (dynamic information, non-dynamic information) uploaded from the client terminal 20 of each medical facility is stored.

In the storage 15, the standard value is stored for each item (diaphragm speed, lung field area change rate, airway diameter stenosis rate, etc.) of the movement information. The standard value is a value set on the basis of the movement information which was obtained by analyzing the dynamic image of the patient that does not have the disease. The standard value is the value or range used as a diagnosis criteria. For example, the standard value is used when determining whether the value of movement information is normal or abnormal.

In the client terminal 20, when there is an access to the medical information management apparatus 10 from the login account (user ID, password) corresponding to each user, the controller 11 refers to the user management table 152 of the storage 15, and determines whether or not the user is the user registered in advance. When the user ID and the password input in the client terminal 20 is registered in the user management table 152, the controller 11 determines that the user corresponding to the user ID is a legitimate user.

The controller 11 provides the requested medical information to the requesting client terminal 20, in response to a browsing request from the client terminal 20.

The controller 11 associates the dynamic information with the non-dynamic information and manages them. The dynamic information is obtained by performing dynamic imaging by radiation to a first subject satisfying a predetermined disease condition. The non-dynamic information is obtained by performing imaging other than dynamic imaging or test to a second subject satisfying a predetermined disease condition. That is, the controller 11 functions as a manager.

For example, as the "predetermined disease condition", "not having the predetermined disease" can be used. In this case, the first subject satisfying the predetermined disease condition does not have the predetermined disease, and the second subject satisfying the predetermined disease condition does not have the predetermined disease.

As the "predetermined disease condition", "having the predetermined disease" can be used. In this case, the first subject satisfying the predetermined disease condition has the predetermined disease, and the second subject satisfying the predetermined disease condition has the predetermined disease.

The first subject and the second subject may be different subjects, and may be a same subject. When the "predetermined disease condition" is "no disease", basically, the first the subject and the second the subject are different subjects, since it is unlikely that various imaging and testing would be performed on a patient without disease.

The controller 11 manages the dynamic information and the non-dynamic information in association with each other on the basis of at least one of the disease information, attribute information, information on the imaging site, and the hospital information of the first subject and the second subject.

In the medical information management table 153, the dynamic information and the non-dynamic information are managed in association with each other on the basis of the combination of the disease information, attribute information, imaging site, and hospital information. However, the medical information management table 153 may not include a part of the conditions of the disease information, attribute information, imaging site, and hospital information associating the dynamic information with the non-dynamic information.

The controller 11 manages dynamic information and non-dynamic information in association with each other, the dynamic information being obtained by dynamic imaging with radiation to a first subject that does not have a predetermined disease, and the non-dynamic information being obtained by imaging other than the dynamic imaging or a test to a second subject that does not have the predetermined disease, and the controller 11 manages dynamic information and non-dynamic information in association with each other, the dynamic information being obtained by dynamic imaging to a third subject that has the predetermined disease, and the non-dynamic information being obtained by imaging other than the dynamic imaging or a test to a fourth subject that has the predetermined disease.

The communication unit 14 receives a request from the external device. That is, the communication unit 14 functions as a receiver.

The controller 11 outputs, to the external device, the dynamic information obtained by dynamic imaging with radiation to the first subject that satisfies the predetermined disease condition on the basis of the request. That is, the controller 11 functions as an outputter. To "output dynamic information to the external device" includes causing the external device to display the dynamic information, sending the dynamic information as data to the external device, etc.

The controller 11 outputs, to the external device, the non-dynamic information obtained by imaging other than dynamic imaging or a test to the second subject that satisfies the predetermined disease condition on the basis of the request. To "output non-dynamic information to the external device" includes causing the external device to display the non-dynamic information, sending the non-dynamic information as data to the external device, etc.

Figure 5:
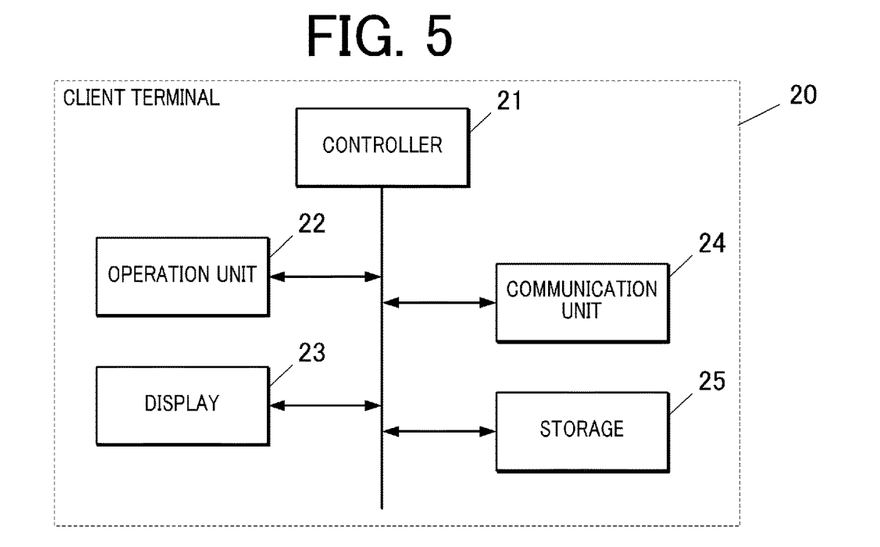
FIG. 5 is a block diagram showing the functional configuration of a client terminal.

FIG. 5 shows the functional configuration of the client terminal 20.

As shown in FIG. 5, the client terminal 20 is configured by including a controller 21, an operation unit 22, a display 23, a communication unit 24, a storage 25, etc. The components are connected via a bus.

The controller 21 is configured by including a CPU, a RAM, etc., and integrally controls the processing operations of the components in the client terminal 20. The CPU of the controller 21 reads out system programs and various processing programs stored in the storage 25 to loads them into the RAM, and executes various processing in accordance with the loaded programs.

The operation unit 22 is configured by including a keyboard including cursor key, character and numeral input keys and various function keys, and a pointing device such as a mouse. The operation unit 22 outputs the instruction signals input by the key operation to the keyboard and mouse operation to the controller 21. The operation unit 22 may include a touch panel on the display screen of the display 23. In this case, the operation unit 22 outputs the instruction input via the touch panel to the controller 21.

The display 23 is configured by a monitor such as an LCD, and displays various screens in accordance with the instruction of the display signal input from the controller 21. For example, the display 23 displays various web screens on the basis of the display data of various web screens received from the medical information management apparatus 10.

The communication unit 24 is configured by a network interface or the like, and performs data transmission and reception with external devices connected via the communication network N such as the internet.

The storage 25 is composed of HDD, SSD, etc., and stores various processing programs, parameters and files necessary for execution of said programs, etc. For example, the storage 25 stores a web browser program to realize a web browser.

[Operation of Medical Information Management System]

Next, the operation of the medical information management system 100 will be described.

Figure 6:
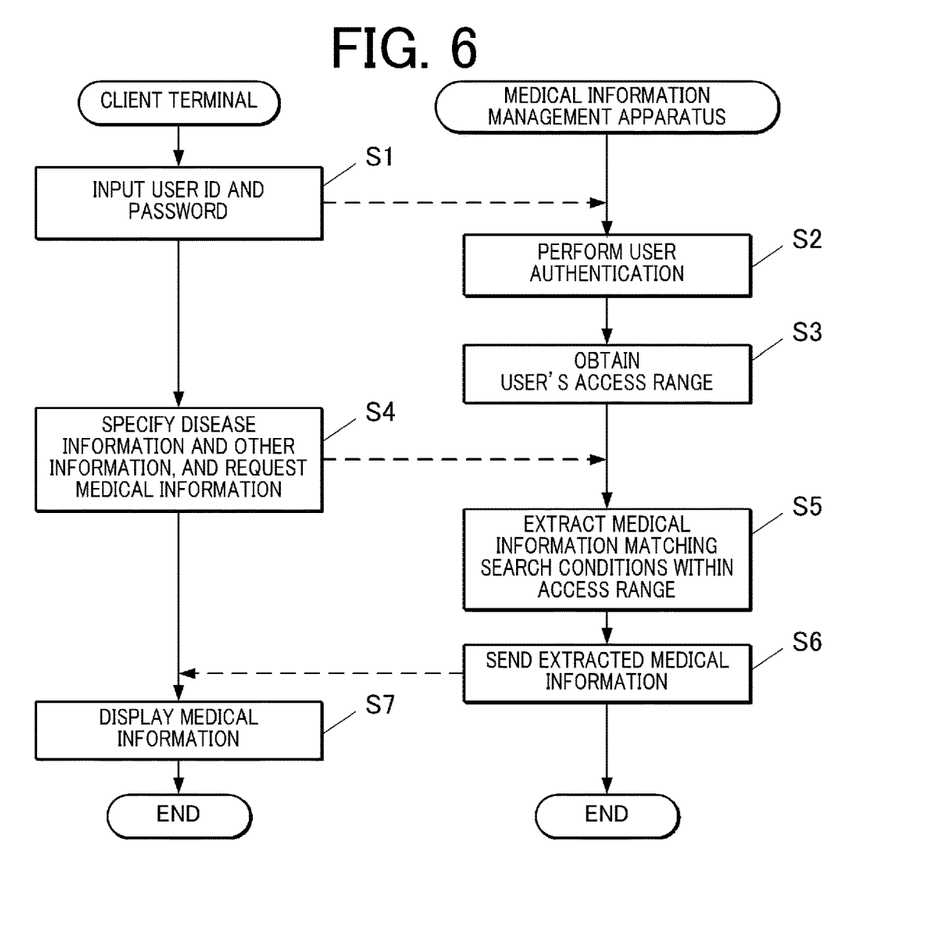
FIG. 6 is a ladder chart showing medical information providing processing executed by the client terminal and the medical information management apparatus.

FIG. 6 is a ladder chart showing medical information providing processing executed by the client terminal 20 and the medical information management apparatus 10. The processing in the medical information management apparatus 10 is achieved by software processing by cooperation between the CPU of the controller 11 and the medical information management program 151 stored in the storage 15. The processing in the client terminal 20 is achieved by software processing by cooperation between the CPU of the controller 21 and the program stored in the storage 25. This processing is performed, for example, when a medical worker (user) at a medical facility browses medical information on a subject under the same or similar conditions as the diagnosis target image, as a diagnostic reference for newly captured dynamic image.

First, at the client terminal 20, when the user operates the operation unit 22 and enters the URL to access the medical information management apparatus 10 from a web browser, the controller 21 accesses the medical information management apparatus 10 via the communication unit 24 based on the inputted URL.

In the medical information management apparatus 10, the controller 11 sends display data for displaying the login screen to the client terminal 20 via the communication unit 14. The data for displaying various Web screens, including the login screen, sent to the client terminal 20 by the Web server function of the medical information management apparatus 10 includes HTML, style sheets, image data, and scripts for executing predetermined processing on client terminal 20, etc.

In the client terminal 20, the login screen is displayed on the display 23. The login screen includes the input region of user ID and password. In the login screen, when the user operates the operation unit 22 to input the user ID and password (step S1), the controller 21 sends the input user ID and password to the medical information management apparatus 10 via the communication unit 24.

In the medical information management apparatus 10, when the user ID and the password are received by the communication unit 14, the controller 11 performs user authentication (step S2). To be specific, the controller 11 searches for the record matching the received user ID from the user management table 152 of the storage 15, and determines that the user authentication was successful when the received password matches the password included in the searched record.

Next, the controller 11 obtains the access range of user from the user management table 152 (step S3). To be specific, the controller 11 refers to the user management table 152, and obtains the access authority to the dynamic image, movement information, medical image (non-dynamic image) and the test result in non-dynamic information, etc. of the user during login.

The controller 11 sends display data for displaying the search condition specification screen via the communication unit 14 to the client terminal 20.

In the client terminal 20, the search condition specification screen is displayed on the display 23. The search condition specification screen includes the specification region for specifying the disease information, attribute information, imaging site and hospital information. In the search condition specification screen, when the user operates the operation unit 22 and specifies the disease information, attribute information, imaging site and hospital information, the controller 21 sends the request of medical information satisfying the specified search conditions to the medical information management apparatus 10 via the communication unit 24 (step S4).

For example, the search conditions such as "no disease" as "disease information", "30s, male" as "attribute information", "chest" as "imaging site" and "not specified" as "hospital information" are specified.

The search conditions such as "COPD" as "disease information", "having a smoking history" as "attribute information", "chest" as "imaging site" and "department of internal medicine" as "hospital information" are specified.

When the medical information management apparatus 10 receives a request including the search conditions by the communication unit 14, the controller 11 extracts the medical information matching the search conditions within the access range which is allowed for the user, from the medical information management table 153 of the storage 15 (step S5).

The controller 11 sends the display data for displaying the extracted medical information to the client terminal 20 via the communication unit 14 (step S6).

The client terminal 20 displays the medical information on the display 23 (step S7). The user browses the medical information displayed on the display 23.

In the client terminal 20, the user may operate the operation unit 22 to select the medical information to be downloaded from among the pieces of medical information displayed on the display 23 so as to download the selected medical information from the medical information management apparatus 10 (store the medical information in the client terminal 20 or in any other device in the medical facility).

Then, the medical information providing processing ends.

Figure 7:
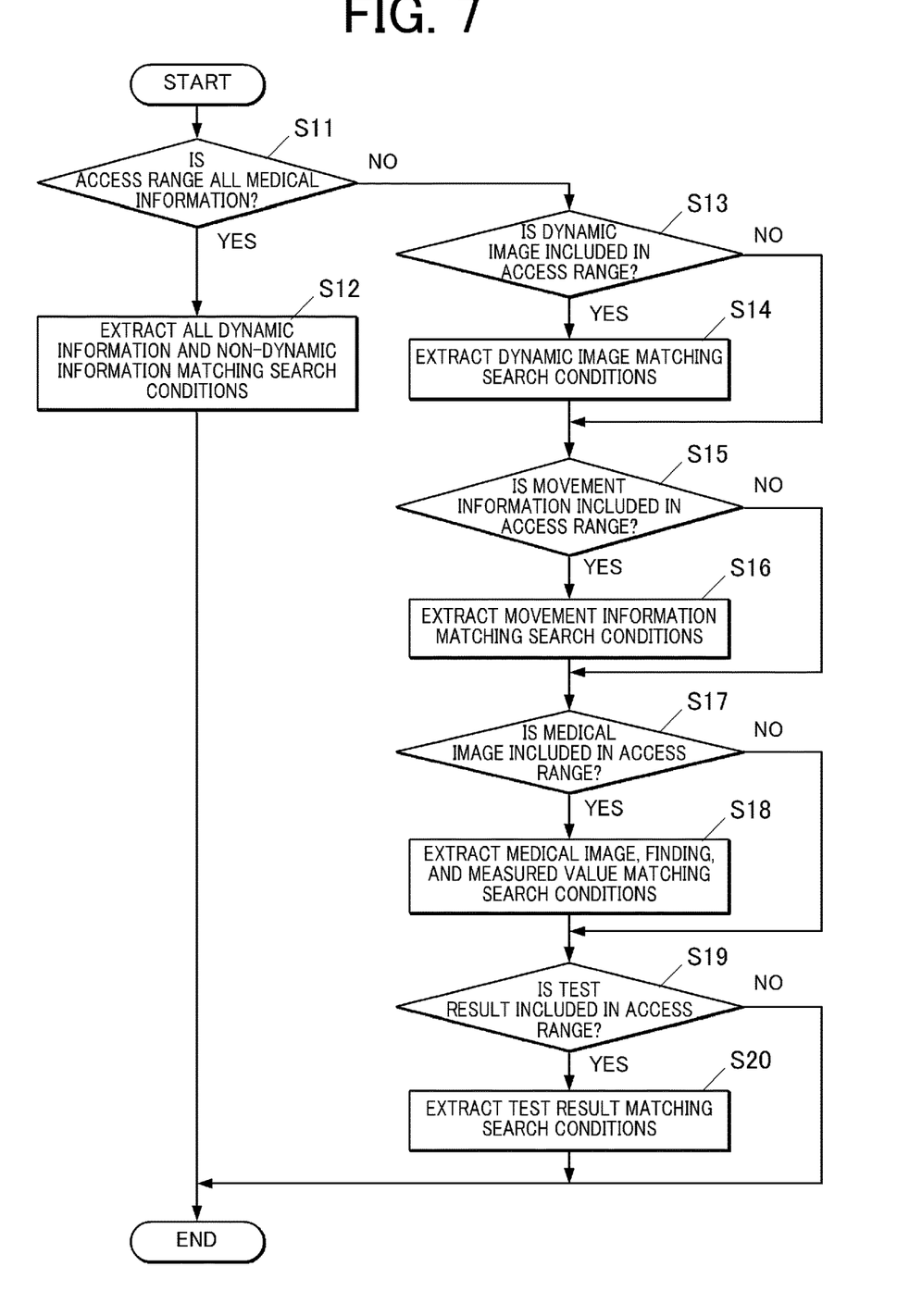
FIG. 7 is a flowchart showing medical information extraction processing executed by the medical information management apparatus.

FIG. 7 is a flowchart showing medical information extraction processing executed by the medical information management apparatus 10. The medical information extraction processing is described for detailed description of step S5 of the medical information providing processing (see FIG. 6).

The controller 11 of the medical information management apparatus 10 determines whether or not the access range of the user obtained in step S3 of the medical information providing processing is all the medical information (step S11).

If the access range of the user is all the medical information (step S11; YES), the controller 11 extracts all the dynamic information and non-dynamic information matching the search conditions (combination of disease information, attribute information, imaging site, and hospital information) from the medical information management table 153 of the storage 15 (step S12). To be specific, the controller 11 sets, as the target to be extracted, all of the dynamic information (dynamic image, movement information) and non-dynamic information (medical image for each modality, finding, measured value, test result for each test) included in the record corresponding to the combination of disease information, attribute information, imaging site and hospital information specified by the user in the medical information management table 153. The dynamic image is obtained from the data storage region 154 of the storage 15 on the basis of the identification information of the dynamic image. The medical image (non-dynamic image) in the non-dynamic information is obtained from the data storage region 154 on the basis of the identification information of the medical image.

In step S11, if the access range of the user is not all the medical information (step S11; NO), the controller 11 determines whether or not the dynamic image is included in the access range of the user (step S13).

If the dynamic image is included in the access range of the user (step S13; YES), the controller 11 extracts the dynamic image matching the search conditions from the medical information management table 153 (step S14). To be specific, the controller 11 obtains the dynamic image from the data storage region 154 on the basis of the identification information of the dynamic image extracted from the medical information management table 153.

In step S13, if the dynamic image is not included in the access range of the user (step S13; NO), or after step S14, the controller 11 determines whether or not the movement information is included in the access range of the user (step S15).

If the movement information is included in the access range of the user (step S15; YES), the controller 11 extracts the movement information matching the search conditions from the medical information management table 153 (step S16).

In step S15, if the movement information is not included in the access range of the user (step S15; NO), or after step S16, the controller 11 determines whether or not the medical image (non-dynamic image) in the non-dynamic information is included in the access range of the user (step S17).

If the medical image (non-dynamic image) in the non-dynamic information is included in the access range of the user (step S17; YES), the controller 11 extracts the medical image (non-dynamic image), finding, and measured value in the non-dynamic information matching the search conditions from the medical information management table 153 (step S18). The medical image (non-dynamic image) in the non-dynamic information is obtained from the data storage region 154 on the basis of the identification information of the medical image.

In step S17, if the medical image (non-dynamic image) in the non-dynamic information is not included in the access range of the user (step S17; NO), or after step S18, the controller 11 determines whether or not the test result is included in the access range of the user (step S19).

If the test result is included in the access range of the user (step S19; YES), the controller 11 extracts the test result matching the search conditions from the medical information management table 153 (step S20).

In step S19, if the test result is not included in the access range of the user (step S19; NO), after step S20, or after step S12, the controller 11 ends the medical information extraction processing.

When the user that operates the client terminal 20 has the access authority for the dynamic information and non-dynamic information, the controller 11 of the medical information management apparatus 10 sends the display data for displaying the dynamic information and the non-dynamic information matching the search conditions to the client terminal 20 via the communication unit 14.

In the client terminal 20, the dynamic information and the non-dynamic information matching the search conditions are displayed on the display 23. The user can browse the dynamic image and the movement information while comparing them with the test result and the medical image (non-dynamic image) related to imaging other than the dynamic imaging.

When the user that operates the client terminal 20 has the access authority for the movement information, the controller 11 of the medical information management apparatus 10 may obtain the standard value for each item of the movement information from the storage 15, to display the standard value on the display 23 of the client terminal 20 together with the movement information matching the search conditions. The user can browse the movement information while referring to the standard value for each item.

The medical information management apparatus 10 may have an AI (Artificial Intelligence) algorism for determining normality/abnormality and pointing out the disease name in response to reception of dynamic information, etc. which is the diagnosis target. As the learning data to this AI algorism, the data set accumulated in the medical information management table 153 can be used. To be specific, machine learning is performed with the dynamic information and the non-dynamic information as the input data and with the condition of predetermined disease (disease name, no disease, etc.) as the output data. The dynamic information and the non-dynamic information are associated with each other in the medical information management table 153. The dynamic information is obtained by dynamic imaging with radiation to a first subject that satisfies the condition of a predetermined disease. The non-dynamic information is obtained by imaging other than the dynamic imaging or the test to a second subject that satisfies the condition of the predetermined disease. When the dynamic information and the non-dynamic information of the patient (subject) to be diagnosed are input to the identifier generated by this machine learning, whether there is a disease and the disease name are output.

Furthermore, when machine learning is performed, the attribute information, imaging site, hospital information, etc. of the subject may be added to the input data together with the dynamic information and the non-dynamic information. By using the identifier generated by this machine learning, it is possible to output whether there is a disease and the disease name from the dynamic information, non-dynamic information, attribute information, imaging site, hospital information, etc. of the patient (subject) to be diagnosed.

As described above, according to the medical information management apparatus 10 in the embodiment, by associating the dynamic information with the non-dynamic information with which the user is more familiar than the dynamic information, it is possible to facilitate the use of dynamic information.

For example, by displaying the non-dynamic image together with the dynamic image on the display 23 of the client terminal 20, it is possible to provide information regarding how the subject of the same disease condition as that of the dynamic image is captured by imaging other than the dynamic imaging.

Since the dynamic imaging is a relatively new technique, it is possible to make the user recognize the usability of the dynamic information by enabling the user to compare the dynamic information with the information obtained by conventional diagnosis method other than the dynamic imaging, both for the diagnosis and for the clinical study.

In the medical information management table 153, the dynamic information is supported by the objective fact of the non-dynamic information, which increases user trust in the dynamic information and promotes the use of dynamic information.

Since the medical information management table 153 of the medical information management apparatus 10 includes the correspondence between the dynamic information and the non-dynamic information obtained from a normal subject (subject not having the disease), it is possible to provide a normal case of the dynamic information and the non-dynamic information to the user.

Since the medical information management table 153 of the medical information management apparatus 10 includes the correspondence between the dynamic information and the non-dynamic information obtained from a subject having a predetermined disease, it is possible to provide an abnormal case of the dynamic information and the non-dynamic information to the user for each disease.

The medical information management apparatus 10 can manage the dynamic information and the non-dynamic information in association with each other, on the basis of at least one of disease information (whether there is a disease, disease name), attribute information, information on the imaging site, and the hospital information of the subject.

As for the subject not having a disease, it is difficult to collect the dynamic information and non-dynamic information by performing multiple imagings or tests to the same subject. Thus, it is important to manage the dynamic information and the non-dynamic information of subjects satisfying a same condition for the disease in association with each other even if the subjects are different subjects.

The medical information management apparatus 10 can output, to the client terminal 20, the dynamic information obtained by dynamic imaging with radiation to a first subject that satisfies the condition of the predetermined disease, on the basis of the request from the client terminal 20.

The medical information management apparatus 10 can output, to the client terminal 20, the non-dynamic information obtained by test or imaging other than dynamic imaging to a second subject that satisfies the condition of the predetermined disease, on the basis of the request from the client terminal 20.

The medical information management apparatus 10 can widely publish normal and abnormal cases of dynamic information in response to the request from the client terminal 20 for browsing and downloading of medical information, thereby promoting the dynamic state.

The medical information management apparatus 10 can publish medical information corresponding to the request within the access range which is set to the user.

If there is an AI algorism determining normality/abnormality and disease name for each medical facility, it is necessary to collect data to update the algorism for each medical facility, and the accuracy varies between medical facilities.

In contrast to this, since the medical information management apparatus 10 collects medical information from multiple medical facilities, compared to the case of managing the information for each medical facility, it becomes easy to collect large amount of data, and the difference in accuracy between medical facilities in determination of disease by the AI algorism using the medical information is eliminated.

The description in the embodiment is an example of the medical information management apparatus, data structure of medical information and the medical information management program according to the present invention, and the present invention is not limited to this. As for the detailed configurations and detailed operations of components forming the apparatuses/devices, modifications can be made appropriately within the scope of the present invention.

For example, the data structure of the medical information management table 153 (see FIG. 4) is not limited to the illustrated example, and modifications can be made according to the use.

Instead of the medical information management table 153, the medical information management apparatus 10 may separately have the dynamic information management table managing dynamic information and the non-dynamic information management table managing non-dynamic information. To be specific, the dynamic information management table stores the dynamic information (dynamic image, movement information, etc.) for each combination of the disease information, attribute information, imaging site and hospital information. The non-dynamic information management table stores the non-dynamic information (medical image, finding, measured value, test result, etc.) for each combination of the disease information, attribute information, imaging site and hospital information. In this case, it is possible to provide the dynamic information and the non-dynamic information which are associated by a common search condition to the client terminal 20, by extracting the dynamic information matching the search condition (combination of disease information, attribute information, imaging site and hospital information) from the dynamic information management table and extracting the non-dynamic information matching the search condition from the non-dynamic information management table.

Though the embodiment has been described for a case where the dynamic information includes the dynamic image and the movement information, the dynamic information managed in the medical information management apparatus 10 may not include the movement information, but may include only the dynamic image (medical image obtained by dynamic imaging) By making users aware of the significance of the dynamic image by letting them know the movement of normal and abnormal cases in the dynamic image, it is possible to contribute to the spread of dynamic imaging.

The non-dynamic information managed in the medical information management apparatus 10 may be only the non-dynamic image (medical image obtained by imaging other than the dynamic imaging). By comparing the dynamic image with the non-the dynamic image that the user is familiar with, it is easier to understand the movement of normal and abnormal cases in the dynamic image.

In the user management table 152 (see FIG. 3), the access range of the user may be managed by dividing it into browsing, downloading, etc.

The users who use the medical information in the medical information management apparatus 10 may be charged. For example, use a pay-as-you-go system in which the amount of money is determined based on the amount of medical information (amount of data, number of files, number of times, etc.) browsed or downloaded by the user may be used, or a flat rate within a predetermined period may be used. The user may be charged by the medical facility to which each user belongs. The charging may be performed separately for browsing and downloading.

The programs for executing each processing in each apparatus/device may be stored in a portable storage medium. Carrier wave is also applicable as a medium to provide the data of the program via communication lines.

Although embodiments of the present invention have been described and illustrated in detail, the disclosed embodiments are made for purposes of illustration and example only and not limitation. The scope of the present invention should be interpreted by terms of the appended claims

What is claimed is:

1. A medical information management apparatus comprising a hardware processor that manages dynamic information and non-dynamic information in association with each other, the dynamic information being obtained by dynamic imaging with radiation to a first subject that satisfies a condition of a predetermined disease, and the non-dynamic information being obtained by imaging other than the dynamic imaging or a test to a second subject that satisfies the condition of the predetermined disease, the second subject being different from the first subject,
  wherein the hardware processor is connectable to client terminals through a network to enable data communication,
  the hardware processor is configured to authenticate a user using a requesting client terminal and obtain an access range of the user, and
  the hardware processor is configured to provide in response to a browsing request from the user using the requesting client terminal of the client terminals the dynamic information and the non-dynamic information to the requesting client terminal, based on search conditions of the browsing request and based on the access range of the user.

2. The medical information management apparatus according to claim 1, wherein the first subject that satisfies the condition of the predetermined disease does not have the predetermined disease, and the second subject that satisfies the condition of the predetermined disease does not have the predetermined disease.

3. The medical information management apparatus according to claim 2, wherein the hardware processor manages dynamic information and non-dynamic information in association with each other, the dynamic information being obtained by dynamic imaging to a third subject that has the predetermined disease, and the non-dynamic information being obtained by imaging other than the dynamic imaging or a test to a fourth subject that has the predetermined disease.

4. The medical information management apparatus according to claim 1, wherein the first subject that satisfies the condition of the predetermined disease has the predetermined disease, and the second subject that satisfies the condition of the predetermined disease has the predetermined disease.

5. The medical information management apparatus according to claim 1, wherein the dynamic information is a medical image.

6. The medical information management apparatus according to claim 1, wherein the non-dynamic information is a medical image.

7. The medical information management apparatus according to claim 6, wherein the medical image in the non-dynamic information includes at least one of a first medical image and a second medical image, the first medical image being obtained from at least one of fluoroscopic imaging and still image imaging with radiation, and the second medical image being obtained by imaging other than imaging with radiation.

8. The medical information management apparatus according to claim 1, wherein the non-dynamic information includes at least one of a test report and a test result obtained by the test not accompanied by an image.

9. The medical information management apparatus according to claim 1, wherein the hardware processor manages the dynamic information and the non-dynamic information in association with each other, based on at least one of disease information, attribute information, information on an imaging site, and hospital information of the first subject and the second subject.

10. The medical information management apparatus according to claim 9, wherein the attribute information does not include information identifying a person.

11. The medical information management apparatus according to claim 9, wherein
  the disease information is information on a disease that the first subject and second subject has,
  the attribute information does not identify the first subject and the second subject and is selected from the group consisting of information consisting of gender, the birth date, the age, the height, BMI, race, history of smoking, and combinations thereof,
  the imaging site is information indicating a site of the imaging target on the first subject and the second subject, and
  the hospital information is information indicating a medical facility where the imaging or test was performed on the first subject and the second subject.

12. The medical information management apparatus according to claim 11, wherein the hardware processor manages the dynamic information and the non-dynamic information in association with each other, based on each of the disease information, the attribute information, the information on an imaging site, and the hospital information of the first subject and the second subject.

13. The medical information management apparatus according to claim 1, wherein the dynamic information includes movement information obtained by analyzing a medical image.

14. The medical information management apparatus according to claim 13, wherein the medical image is a dynamic image.

15. The medical information management apparatus according to claim 1, further comprising a receiver that receives the browsing, wherein
  the hardware processor outputs, to the requesting client terminal, the dynamic information obtained by the dynamic imaging with the radiation to the first subject that satisfies the condition of the predetermined disease.

16. The medical information management apparatus according to claim 15, wherein the hardware processor outputs, to the requesting client terminal, the non-dynamic information obtained by the imaging other than the dynamic imaging or the test to the second subject that satisfies the condition of the predetermined disease.

17. A non-transitory computer-readable storage medium storing a medical information management program causing a computer to perform management processing which is managing dynamic information and non-dynamic information in association with each other, the dynamic information being obtained by dynamic imaging with radiation to a first subject that satisfies a condition of a predetermined disease, and the non-dynamic information being obtained by imaging other than the dynamic imaging or a test to a second subject that satisfies the condition of the predetermined disease, the second subject being different from the first subject,
  wherein the medical information management program causes the computer to connect to client terminals through a network to enable data communication,
  authenticate a user using a requesting client terminal and obtain an access range of the user, and
  provide in response to a browsing request from the user using the requesting client terminal of the client terminals the dynamic information and the non-dynamic information to the requesting client terminal, based on search conditions of the browsing request and based on the access range of the user.

* * * * *